US012636141B2

(12) United States Patent
Xiao et al.

(10) Patent No.: US 12,636,141 B2
(45) Date of Patent: May 26, 2026

(54) COVERED STENT

(71) Applicant: Lifetech Scientific (Shenzhen) Co. Ltd., Shenzhen (CN)

(72) Inventors: Benhao Xiao, Shenzhen (CN); Tingbo Ming, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 559 days.

(21) Appl. No.: 18/039,153

(22) PCT Filed: Aug. 13, 2021

(86) PCT No.: PCT/CN2021/112563
§ 371 (c)(1),
(2) Date: May 26, 2023

(87) PCT Pub. No.: WO2022/116593
PCT Pub. Date: Jun. 9, 2022

(65) Prior Publication Data
US 2023/0414340 A1      Dec. 28, 2023

(30) Foreign Application Priority Data

Dec. 2, 2020    (CN) .......................... 202011391333.3
Dec. 2, 2020    (CN) .......................... 202011391335.2

(51) Int. Cl.
*A61F 2/07*          (2013.01)
*A61F 2/06*          (2013.01)
(52) U.S. Cl.
CPC .......... *A61F 2/07* (2013.01); *A61F 2002/061* (2013.01); *A61F 2002/067* (2013.01)
(58) Field of Classification Search
CPC .................. A61F 2/07; A61F 2002/061; A61F 2002/067; A61F 2/90; A61F 2002/065;
(Continued)

(56) References Cited

U.S. PATENT DOCUMENTS

2002/0095205 A1*   7/2002   Edwin ........................ A61F 2/07
                                                          600/431
2009/0093873 A1*   4/2009   Navia ........................ A61F 2/07
                                                          623/1.36
(Continued)

FOREIGN PATENT DOCUMENTS

CN         202950795 U     5/2013
CN         106923943 A     7/2017
(Continued)

OTHER PUBLICATIONS

Search Report dated Oct. 2, 2024 for corresponding European Application No. 21 89 9629.
(Continued)

*Primary Examiner* — Suzette J Gherbi
(74) *Attorney, Agent, or Firm* — Raymond Sun

(57)          ABSTRACT

A covered stent (10), comprising a main body stent (11), a window (13) being formed on a surface of the main body stent (11). The covered stent (10) further includes an internal covering film (14). An edge of the internal covering film (14) is connected to the main body stent (11). The internal covering film (14) includes a bottom portion (141), a proximal end folding portion and a distal end folding portion, and the proximal and distal end folding portions are disposed at two ends of the bottom portion (141), respectively. At least one of the proximal end folding portion and the distal end folding portion is disposed on an inner surface of the main body stent (11), and is recessed toward an inner cavity of the main body stent (11) to form a receiving cavity, and a through hole (147) that communicates with the inner cavity of the main body stent (11) is also formed on the internal covering film (14). The internal covering film (14) of the covered stent (10) is provided with folding portions (142), and the folding portions (142) have a receiving cavity. When an implantation path of a bridging stent (100) is established,
(Continued)

a guide wire or catheter can extend into a branch stent (12) along the receiving cavity, to thereby quickly establish the implantation path of the bridging stent (100) and shorten the operation time.

20 Claims, 14 Drawing Sheets

(58) Field of Classification Search
CPC ........ A61F 2002/825; A61F 2230/0067; A61F 2250/0039
See application file for complete search history.

(56) References Cited

U.S. PATENT DOCUMENTS

| | | | |
|---|---|---|---|
| 2013/0211506 A1 | 8/2013 | Dake et al. | |
| 2014/0277347 A1 | 9/2014 | Daugherty et al. | |
| 2017/0340462 A1* | 11/2017 | Lostetter ................... | A61F 2/07 |
| 2020/0170778 A1* | 6/2020 | Ehnes ....................... | A61F 2/88 |
| 2020/0352698 A1 | 11/2020 | Hidari et al. | |
| 2021/0000585 A1* | 1/2021 | Palermo .................... | A61F 2/07 |
| 2022/0079783 A1* | 3/2022 | Wang ....................... | A61F 2/856 |
| 2023/0372079 A1* | 11/2023 | Moore ...................... | A61F 2/07 |

FOREIGN PATENT DOCUMENTS

| | | |
|---|---|---|
| CN | 109152639 A | 1/2019 |
| CN | 109833115 A | 6/2019 |
| CN | 109938895 A | 6/2019 |
| CN | 110507448 A | 11/2019 |
| EP | 2 465 471 B1 | 5/2016 |

OTHER PUBLICATIONS

Office action dated Mar. 12, 2025 in corresponding China Appl. No. 202011391335.2.
Office action dated Mar. 10, 2025 in corresponding China Appl. No. 202011391333.3.
International Search Report dated Nov. 18, 2021 for corresponding PCT Application No. PCT/CN2021/112563.

* cited by examiner

A

656

657

75

751

(a)

(b)

(c)

COVERED STENT

TECHNICAL FIELD

The present disclosure relates to the technical field of medical instruments, specifically to a covered stent.

BACKGROUND ART

Aortic aneurysms and aortic dissections are currently serious diseases endangering the safety of human life. Without treatment, the aortic aneurysm and dissection will continue to expand and eventually rupture, causing serious complications and death. With the increasing number of patients suffering from hypertension, hyperlipidemia and hyperglycemia, the incidence rate of aortic aneurysm and aortic dissection is also increasing significantly.

Traditional invasive surgery for treating aortic aneurysm and aortic dissection is characterized by large trauma, high mortality, long operation time, high incidence of postoperative complications and high surgical difficulty. An endovascular therapy has become the current main method for treating aortic aneurysm and aortic dissection gradually due to its characteristics of lesser trauma, fewer postoperative complications, short operation time, low surgical difficulty and the like. By means of implanting a covered stent in the aorta, the vascular lesion is isolated outside the covered stent, and the blood flow is restricted from flowing through the covered stent, so as to protect the blood vessel. In order to ensure the implantation fixation of covered stents and prevent the blood flow from flowing into the blood vessel through the proximal and distal ends of the stents, the covered stents need to have an anchoring region with a certain length. Therefore, when aortic aneurysm or dissection involves a branch artery, and a covered stent is implanted for treatment, the branch artery will be blocked to varying degrees or even an endovascular technology cannot be implemented.

For the endovascular treatment of aortic aneurysms or dissections involving branch arteries, in order to achieve blood circulation of the branch arteries, a fenestrated stent technology and a chimney stent technology are often used. The fenestrated stent technology is to perform in vitro or in situ fenestration on a covered stent to create a side hole on the covered stent. The position of the side hole corresponds to an incision position of the branch artery. During the operation, the stent is implanted, the side hole is aligned with the branch artery, and then a bridging stent is implanted through the branch artery to cooperate with the covered stent. The chimney stent technology means that after the implantation of a covered stent, a bridging stent is implanted through the branch artery to cooperate with the covered stent. In general, the fenestrated stent technology has high locating difficulty. Customization of a stent takes a long time, and the stent cannot be used for emergency treatment. The chimney stent technology easily causes internal hemorrhage. Furthermore, due to the limitations caused by the vascular anatomy, it is difficult to reconstruct a multi-branch artery. At the same time, whether the fenestrated stent technology or the chimney stent technology is used, the branch artery is always ischemic before the branch artery is reconstructed, and the probability of postoperative complications is high.

SUMMARY OF THE DISCLOSURE

For the above problems, the present disclosure provides a covered stent, including a main body stent, a window being formed on a surface of the main body stent; the covered stent further includes an internal covering film; an edge of the internal covering film is connected to the main body stent; the internal covering film includes a bottom portion, a proximal end folding portion and a distal end folding portion, and the proximal end folding portion and distal end folding portions are disposed at two ends of the bottom portion, respectively; at least one of the proximal end folding portion and the distal end folding portion is disposed on an inner surface of the main body stent, and is recessed toward an inner cavity of the main body stent to form a receiving cavity; and a through hole that communicates with the inner cavity of the main body stent is also formed on the internal covering film.

In one embodiment, the through hole is arranged at a bottom portion of the receiving cavity, and the folding portion has an opening opposite to the through hole.

In one embodiment, the covered stent also includes a stiffener; and the stiffener is at least partially arranged around the opening to support the opening of the folding portion.

In one embodiment, the stiffener is bent away from and/or close to a center of the opening.

In one embodiment, the main body stent includes a main body supporting member, and an edge of an opening of the receiving cavity partially overlaps the main body supporting member.

In one embodiment, the stiffener includes a suture; the opening of the folding portion includes an upper edge; and the upper edge and an edge of the window are sutured through the suture.

In one embodiment, two ends of the covered stent are provided with openings; the receiving cavity includes an opening and a through hole; the opening of the receiving cavity is opposite to the openings of the covered stent; and the size of the receiving cavity gradually decreases along the direction from the opening of the folding portion to an opening of the covered stent.

In one embodiment, the covered stent also includes a branch stent; and the branch stent is arranged inside the covered stent and communicates with the through hole of the internal covering film.

In one embodiment, the branch stent includes a flared section; and the flared section is connected with the internal covering film.

In one embodiment, the branch stent is a sheet structure with an arc surface; the branch stent has a C-shaped cross section and is arranged on an inner surface of the main body stent; and a space enclosed by the branch stent and the inner surface of the main body stent constitutes an inner cavity of the branch stent.

In one embodiment, one end of the branch stent is provided with an opening, and the other end is provided with two openings; and an end portion of the branch provided with one opening is connected with the internal covering film.

In one embodiment, the covered stent further includes a window supporting member; the window supporting member is arranged outside the internal covering film and protrudes outwardly from a surface of the internal covering film; the window supporting member includes a net structure with meshes, and the size of each mesh can change by an external force.

A covered stent includes a main body covering film, a window being formed on a surface of the main body covering film; the covered stent further includes an internal covering film; an edge of the internal covering film is connected with the main body covering film; the window includes a first edge and a second edge extending along a longitudinal direction of the covered stent; and the internal covering film and the main body covering film are spliced and connected after being formed separately.

In one embodiment, the internal covering film includes a bottom portion located between the first edge and the second edge; the internal covering film is provided with a supporting unit; and the supporting unit makes the bottom portion at least partially protrude outwardly or partially recessed relative to a plane where the first edge and the second edge are located, or parallel to the plane.

In one embodiment, the supporting unit includes a suture; and the suture bypasses the first edge and an edge of the internal covering film, passes through upper and lower surfaces of the internal covering film to the second edge, then bypasses the second edge and the other edge of the internal covering film, and then is connected with the internal covering film and the main body stent.

In one embodiment, the elongation of the internal covering film is greater than 0.01 and less than 0.1.

In one embodiment, the supporting unit includes a waveform supporting structure; and the waveform supporting structure is connected with the surface of the internal covering film.

In one embodiment, the covered stent further includes a window supporting member; the window supporting member is arranged outside the internal covering film and protrudes outwardly from the surface of the internal covering film; and the waveform supporting structure is integrally formed with the window supporting member.

In one embodiment, the internal covering film includes a bottom portion, a proximal end folding portion and a distal end folding portion; the proximal end folding portion and the distal end folding portion are arranged at two ends of the bottom portion; at least one of the proximal end folding portion and the distal end folding portion is arranged on an inner surface of the main body covering film; the supporting unit is arranged at the bottom portion; and the folding portion is closer to a central axis of the covered stent than the bottom portion.

In one embodiment, a sinking section is formed on a surface of the window supporting member, and an area of the cross section of the covered stent where the sinking section is located is smaller than areas of cross sections of other portions of the covered stent far from the sinking section.

In one embodiment, the covered stent further includes a main body supporting member; the main body supporting member is connected with the main body covering film; the window supporting member is a part of the main body supporting member; and on the same cross section, the circumferential ratio of the window supporting member is less than the circumferential ratio of the main body supporting member.

In one embodiment, the window supporting member includes a net structure with meshes, and the size of each mesh can change by an external force.

In one embodiment, a proximal end and/or distal end of the window supporting member extends beyond an edge of the window in the longitudinal direction of the covered stent.

The covered stent provided by the present disclosure can effectively isolate the aortic dissection and aortic aneurysm involving a branch artery of the aorta, effectively reconstruct the blood circulation of the branch artery and avoid long-term ischemia of the branch artery, has low operation difficulty, has no need for customization, and can be applied to emergency treatment.

DETAILED DESCRIPTION OF THE DISCLOSURE

In order to better understand the concept of the present disclosure, the following implementations of the present disclosure are described in combination with the accompanying drawings. The following specific embodiments are only part of the embodiments of the present disclosure, not a limitation of the present disclosure.

For the covered stent of the present disclosure, one end of blood inflow is defined as "proximal end" and one end of blood outflow is defined as "distal end". That is, in use, the blood flows from the proximal end of a covered stent to the distal end.

Embodiment I

Figure 1:
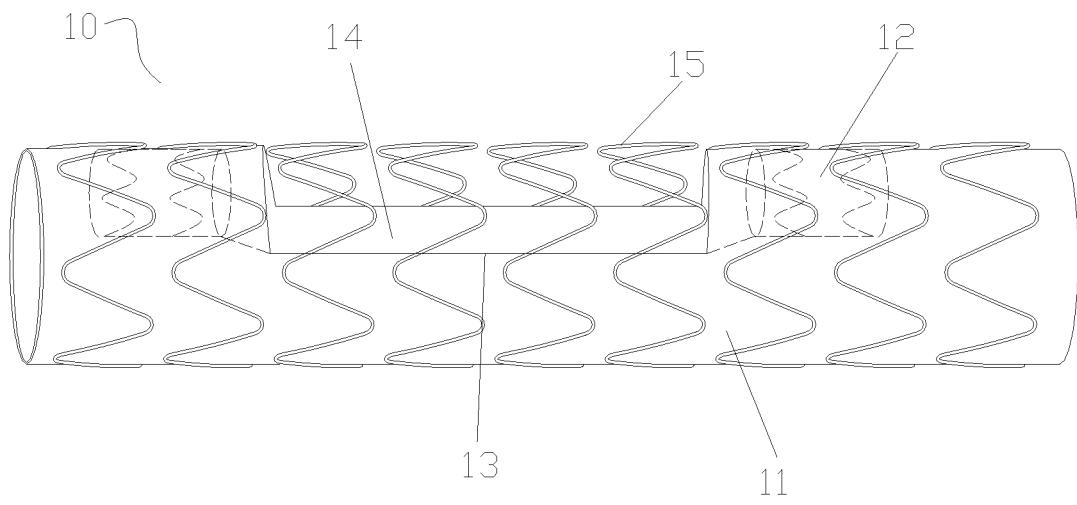
FIG. 1 is a schematic structural diagram of an entire covered stent according to one embodiment of the present disclosure, including a main body stent, a branch stent and an internal covering film.
Figure 3:
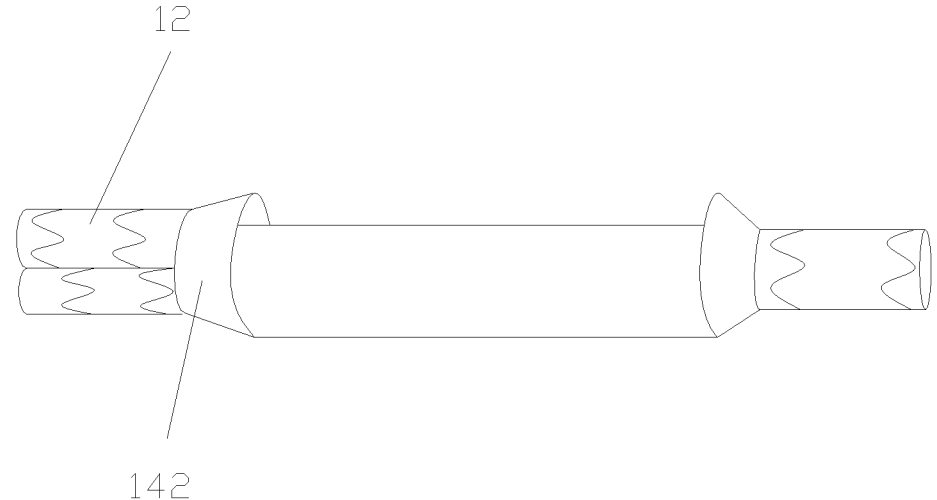
FIG. 3 is a schematic diagram after the internal covering film and the branch stent in the covered stent shown in FIG. 1 are connected.

As shown in FIG. 1, an entire covered stent 10 of this embodiment is a hollow tubular structure with openings at both ends, including a main body stent 11, a branch stent 12, an internal covering film 14 and a window supporting member 15. A window 13 is arranged on a surface of the main body stent 11. An edge of the internal covering film 14 is connected with the main body stent 11. The window supporting member 15 is arranged outside the internal covering film 14 and protrudes outwardly from the surface of the internal covering film 14. A through hole which communicates with an inner cavity of the covered stent 10 is formed in the internal covering film 14. As shown in FIG. 3, the branch stent 12 has a hollow cylindrical structure, which is arranged inside the covered stent 10 and communicates with the through hole on the internal covering film 14, so that blood can flow into a branch vessel through the branch stent 12. In this embodiment, the covered stent 10 includes three branch stents 12. Two branch stents 12 are arranged near the proximal end of the window 13, and one branch stent 12 is arranged near the distal end of the window 13.

Figure 2:
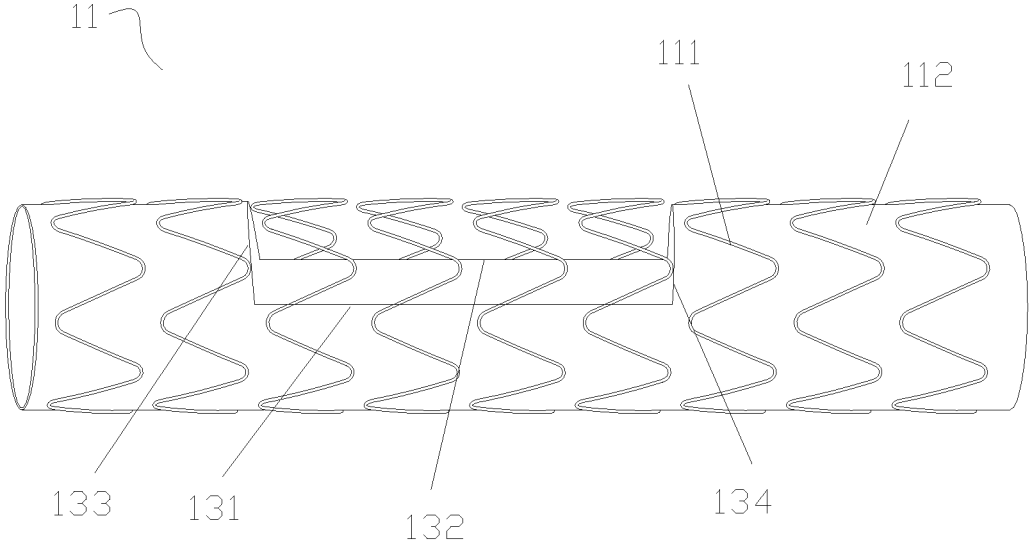
FIG. 2 is a schematic structural diagram of the main body stent in the covered stent shown in FIG. 1.

As shown in FIG. 2, the main body stent 11 includes a main body supporting member 111 and a main body covering film 112, and the main body supporting member 111 is arranged on a surface of the main body covering film 112. It should be understood that the main body supporting member 111 can be arranged on an inner surface of the main body covering film 112 or on an outer surface of the main body covering film, or part of the main body supporting member is arranged on the outer surface of the main body covering film, and the other part of the main body supporting member is arranged on the inner surface of the main body covering film.

The window 13 is formed in the main body covering film 112 and is located in the middle of the main body covering film 112; that is, the main body supporting member 111 and the main body covering film 112 are also arranged between an end portion of the window 13 and an end portion of the main body stent 11. In this embodiment, an edge of the window 13 formed on the main body covering film 112 is rectangular, that is, when the main body covering film 112 spreads along a generatrix that does not pass through the window, the window 13 is rectangular. The window 13 has a first edge 131, a second edge 132, a third edge 133, and a fourth edge 134, and the four edges are enclosed to form the window 13. The first edge 131 and the second edge 132 are opposite and consistent with a longitudinal direction of the covered stent 10, and the third edge 133 and the fourth edge 134 are opposite and closer to end portions of the covered stent 10 than the first edge 131 and the second edge 132. It can be understood that in other embodiments, the window can also be of other shapes, as long as the first edge and the second edge extend along the longitudinal direction of the covered stent, for example, forming a certain angle (for example, the window is trapezoidal) relative to the longitudinal direction of the covered stent, or the first edge and the second edge are arc-shaped (for example, the window is similarly elliptical). The present disclosure does not make restrictions on the specific shape of the window. It can also be understood that the window can be close to the proximal end of the covered stent or the distal end of the covered stent.

Figure 4:
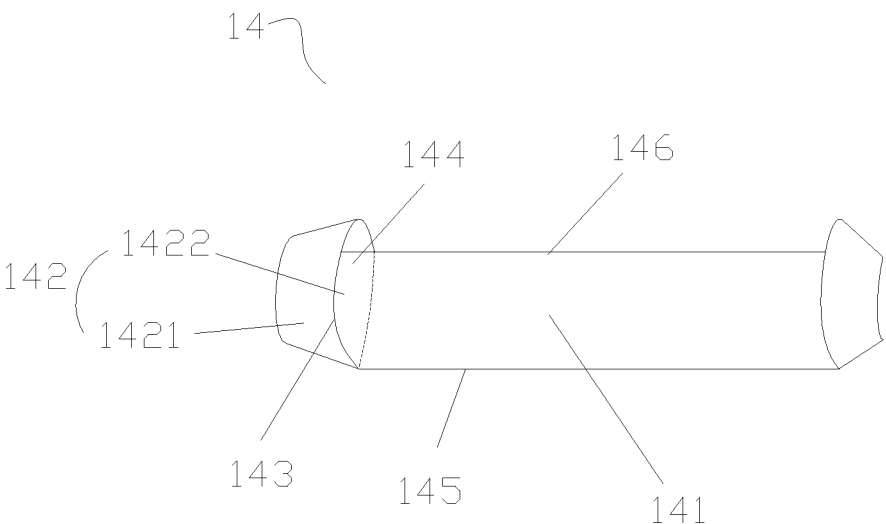
FIG. 4 is a schematic structural diagram of the internal covering film in the covered stent shown in FIG. 1.

As shown in FIG. 1 and FIG. 4, the covered stent 10 in this embodiment includes the internal covering film 14, and an edge of the internal covering film 14 is connected with an edge of the window. Specifically, the internal covering film 14 includes a bottom portion 141 and folding portions 142. The folding portions 142 are arranged at end portions of the bottom portion 141. The folding portions 142 are arranged on an inner surface of the main body stent, and the folding portions 142 are recessed toward an inner cavity of the main body stent 11 to form a receiving cavity 144. The receiving cavity 144 has an upper edge 143. The upper edge 143 is connected with the third edge 133 of the window 13. Specifically, each folding portion 142 includes an upper folding unit 1421 and a lower bottom portion unit 1422 connected with the bottom portion 141. The upper folding unit 1421 and a side edge of the lower bottom portion unit 1422 are connected and are enclosed to form the receiving cavity 144.

It can be understood that in other embodiments, the edge of the internal covering film can also be connected with the inner surface of the main covering film.

Figure 5:
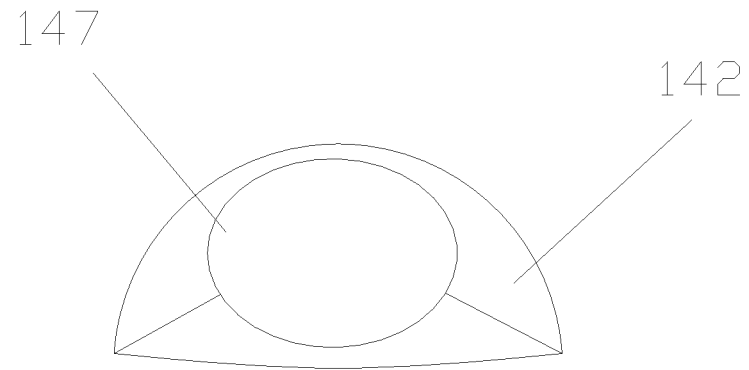
FIG. 5 is a side view of the internal covering film shown in FIG. 4.

As shown in FIG. 5, the internal covering film 14 is also provided with a through hole 147 connected with the inner cavity of the main body stent. The through hole 147 is opposite to an opening of the covered stent 10 and an opening of the receiving cavity 144. Since the folding portion is provided with the receiving cavity, when establishing an implantation path of a bridging stent, a guide wire or catheter can extend into the branch stent along the receiving cavity, to thereby quickly establish the implantation path of the bridging stent and shorten the operation time.

Referring to FIG. 4 again, the internal covering film 14 of this embodiment is provided with two folding portions 142 (including a proximal end folding portion and a distal end folding portion which are respectively arranged at the proximal end and the distal end of the internal covering film), and both folding portions 142 are provided with the through holes 147. The proximal end folding portion 142 is provided with two through holes, and the distal end folding portion 142 is provided with one through hole. In this embodiment, the folding portions are formed by folding back the end portions of the internal covering film 14, specifically by folding the end portions of the internal covering film 14 away from the bottom portion 141 and toward the inner surface of the main body stent 11. It can be understood that the structures of the two folding portions in this embodiment can be identical or slightly different.

When the covered stent of the present disclosure is applied to a curved blood vessel, in order to reduce a tension on the internal covering film caused by the bending of the blood vessel, an included angle between the extending direction of a braided wire of the internal covering film and the length extending direction of the covered stent can be set to be greater than 0 degree.

It can be understood that in other embodiments, the internal covering film can only be provided with the folding portion at the proximal end, and the number of through holes can be 1 to 3. In the present disclosure, the position and number of the branch stent 12 correspond to the position and number of the through hole. That is, when one end of the internal covering film is provided with a plurality of through holes, correspondingly, this end of the internal covering film is also provided with the same number of branch stents 12. The through holes can be staggered, or can be arranged on the same cross section perpendicular to a central axis of the covered stent.

It can also be understood that in other embodiments, the folding portions with the receiving cavities can be separately made into pocket like structures with the receiving cavity and then connected with the bottom portion and the edge of the window respectively.

It can also be understood that in other embodiments, only one folding portion is provided with the receiving cavity, and the other folding portion is only just a slope transitioned from the bottom portion to the inner surface of the main body stent. Of course, at this time, a through hole can still be arranged on this slope. It can be also understood that a through hole can also be arranged on the bottom portion.

In this embodiment, the internal covering film 14 and the main body covering film 112 are separately formed and then connected by a suture. In other embodiments, the two covering films can also be connected by means of adhesion or in other ways. Since the internal covering film is also provided with the branch stent, the internal covering film and the main body covering film can be spliced after being formed separately, which can greatly reduce the manufacturing difficulty. It can be understood that in other embodiments, when the internal covering film is not provided with the folding portion and the branch stent, the internal covering film can also be integrally formed with the main body covering film.

Returning to FIG. 4 and FIG. 5 again, the inner cavity (i.e., the size of the receiving cavity) of each folding portion 142 of this embodiment gradually decreases from the opening towards the through hole 147 (i.e., gradually decreases towards the opening in the end portion of the covered stent). In this way, the guide wire can enter the branch stent more quickly along the receiving cavity when a bridging stent is implanted.

Returning to FIG. 1 and FIG. 2 again, the window 13 of the covered stent 10 is also provided with a window supporting member 15. The window supporting member 15 has an arched cross section, is arranged above the internal covering film 14, and protrudes outwardly from a surface of the internal covering film 14. In this embodiment, the window supporting member 15 and part of the main body supporting member 111 are integrally formed. That is, the window supporting member 15 is one part of the main body supporting member 111. During manufacturing, the window is first formed on the main body covering film, and then the main body supporting member 111 is connected with the main body covering film. The portion of the main body supporting member exposed from the window is the window supporting member. Preferably, the circumferential ratio of the window supporting member of this embodiment is less than that of the main body supporting member. That is, on the same cross section, the proportion of the window supporting member to the perimeter of the cross section is less than that of the main body supporting member to the perimeter of the cross section. In this way, it can be ensured that the size of the inner cavity of the main body stent is not too small at the position where the internal covering film is provided, so as not to affect the hemodynamics in the aorta. It can be understood that in other embodiments, the circumferential ratio of the window supporting member can also be equal to or greater than that of the main body supporting member.

Figure 6:
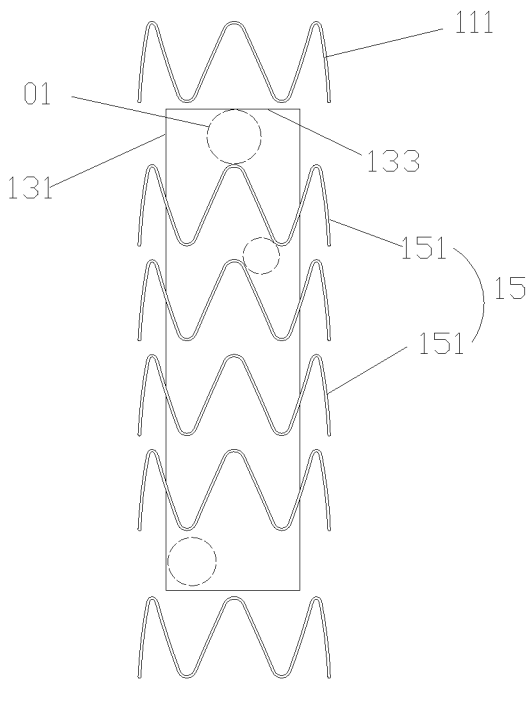
FIG. 6 shows a top view of the covered stent shown in FIG. 1, in which part of the structures are omitted.

As shown in FIG. 6, the window supporting member 15 of this embodiment includes a plurality of supporting sections 151. The plurality of supporting sections 151 is axially spaced apart and connected with the main body stent 11 in a circumferential direction (FIG. 6 only shows part of the structure of the main body stent). In this embodiment, each supporting section 151 includes a plurality of Z-shaped structures connected end to end, and the Z-shaped structures have wave crests and wave troughs, and the axial distance between the wave crests and the wave troughs is a wave height of the Z-shaped structure. In order to better implant the bridging stent into the branch stent and coordinate with the branch stent, and minimize the interference and blockage of the window supporting member to the bridging stent, in the window supporting member 15 of this embodiment, the distance between the wave crest of the supporting section 151 close to the third edge 133 of the window and the third edge 133 is preferably 10 to 20 mm, so that when the bridging stent is implanted, it is not necessary to specifically implant the bridging stent between the wave trough of the supporting section 151 and the third edge 133. Similarly, the distance between the wave trough of the supporting section close to the fourth edge and the fourth edge may also be 10 to 20 mm. It can be understood that in other embodiments, when the bridging stent can be accurately selected to be placed between the wave trough of the supporting section and the third edge, the distance between the wave crest of the supporting section close to the third edge of the window and the third edge may also not be limited. At this time, it can be preferred that the wave height of the supporting section is 6 to 12 mm. In FIG. 6, 01 shows partial optional placement positions of the bridging stent. In other embodiments, the implantation position of the bridging stent can also be optimized by changing the wave height of the supporting section. For example, the wave height of the supporting section close to the third edge and/or the fourth edge can be set to be greater than that of other supporting sections, or a supporting section with a greater wave height can be arranged at a position where the bridging stent needs to be placed, which is not limited to being close to the third edge and the fourth edge.

It can be understood that in other embodiments, two adjacent supporting sections close to the through hole of the internal covering film are of reverse structures. That is, in the two adjacent supporting sections, the wave crest of one supporting section is opposite to the wave trough of the other supporting section. In this way, a position between the opposite wave crest and wave trough can be selected as the implantation position of the bridging stent.

As shown in FIG. 6, in this embodiment, the third edge 133 of the window 13 is located between the window supporting member 15 and the main body supporting member 111, and the upper edge 143 of the folding portion 142 is connected with the third edge 133. At this time, in order to keep the folding portion 142 in a good opening shape, a stiffener can be arranged at the opening of the folding portion 142. For example, sutures can be added or subtracted on the upper edge 143 to properly reduce the deformation capacity of the upper edge 143. It can be understood that in other embodiments, the third edge can also partially overlap the main body supporting member or the window supporting member (that is, the supporting section partially covers the third edge of the window). At this time, an edge of the opening of the receiving cavity (that is, the upper edge) also partially overlaps the main body supporting member or the window supporting member; that is, on a plane parallel to the bottom portion of the internal covering film, projections of the third edge and the upper edge of the receiving cavity both overlap the main body supporting member or the window supporting member. At this time, the main body supporting member or window supporting member can also play a role of supporting the opening of the receiving cavity of the folding portion, which is equivalent to the function of a stiffener. It can also be understood that in other embodiments, the stiffener can also be arranged separately, which will be detailed later.

Figures 7, 8:
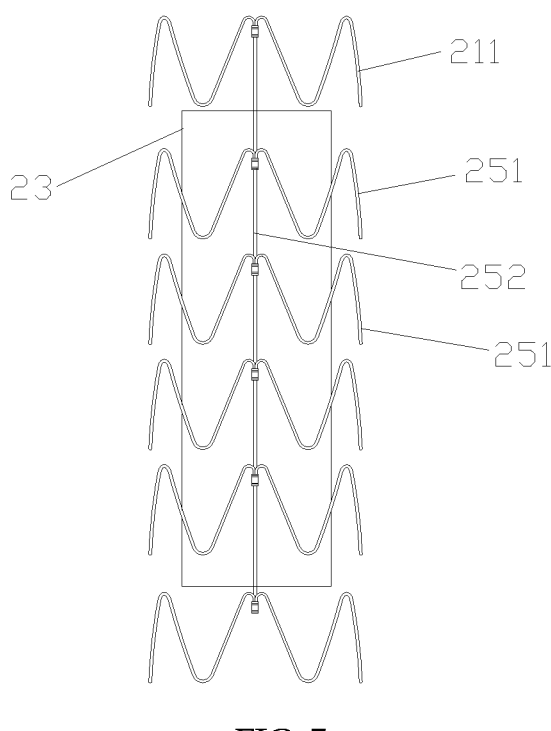
FIG. 7 is a partial schematic structural diagram of a covered stent according to another embodiment of the present disclosure.
FIG. 8 is a partial schematic structural diagram of a covered stent according to still another embodiment of the present disclosure.

In other embodiments, as shown in FIG. 7, the covered stent can also include a connector 252. The connector 252 is arranged above the window 23, and a plurality of supporting sections 251 are connected through the connector 252. In addition, the proximal end and/or the distal end of the connector 252 can extend to the main body supporting member 211 and be connected with the main body supporting member 211. The connector 252 is preferably connected with the wave crests of the adjacent supporting sections 251. More preferably, when the covered stent is implanted into a curved blood vessel, the connector is located exactly on a large curvature side of the covered stent. In this embodiment, the connector 251 is a connecting rod, and the longitudinal direction of the connector 251 is consistent with the extending direction of the covered stent. It can be understood that in other embodiments, the connector can only be connected with the supporting section of the window supporting member, but not extend to the main body stent. The material of the connector can be a medical metal material, such as a superelastic nickel-titanium wire and a medical stainless steel wire. The connector and the supporting section can be connected via crimping or welding. It can be understood that in other embodiments, the connector can also have a certain angle with a longitudinal direction of the covered stent. By means of setting the connector, mutual interference between the supporting sections can be reduced; meanwhile, shortening of the stent can be avoided, and the overall supporting performance of the window supporting member can be improved. When the covered stent is applied to a curved blood vessel, due to the limitation of the connector, the wave crest of the supporting section 251 will not upwarp, so that the covered stent can better adapt to the curvature of the blood vessel.

In other embodiments, as shown in FIG. 8, the connector 352 can include multiple subsections 353. Two adjacent subsections 353 are staggered, and two adjacent supporting sections are connected by one subsection 353. At this time, each subsection 353 can be connected to any position of two adjacent supporting sections. It is preferred that the extending direction of the subsection 353 is consistent with that of the covered stent. Of course, the multiple subsections can also be arranged without staggering, that is, the connector shown in FIG. 7 includes multiple subsections. When the connector includes multiple subsections that are staggered, the selection of the implantation position of the bridging stent is more flexible, and the implanted bridging stent and the branch vessel have a better matching form.

Figure 9:
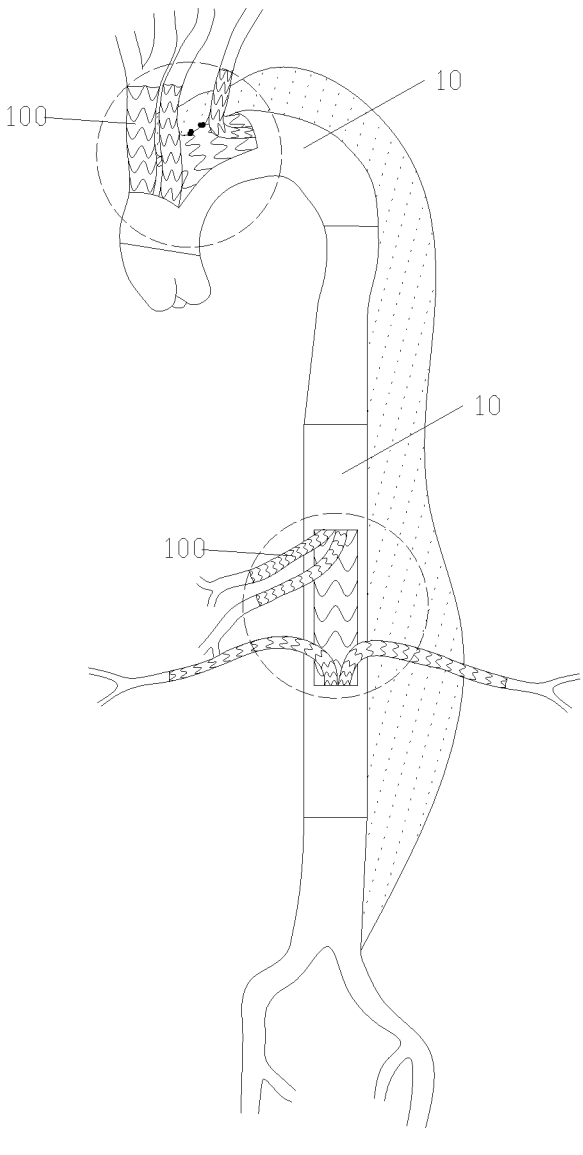
FIG. 9 is a schematic diagram after the covered stent of the present disclosure is implanted into aneurysmal blood vessel.

As shown in FIG. 9, the covered stent 10 of the present disclosure can be used for endovascular treatment of aortic arch aneurysm and treatment of thoracoabdominal aortic aneurysm. Since the window of the covered stent 10 of the present disclosure is provided with the window supporting member, the window supporting member can provide a good radial supporting force. Especially when the covered stent is used for treating the dissecting aneurysm, even if a true lumen is small, the covered stent 10 can also provide a good radial supporting force before the bridging stent 100 is implanted. Especially when the covered stent 10 of the present disclosure is applied to a curved blood vessel, after the covered stent 10 adapts to the shape of the blood vessel and bends, due to the existence of the window supporting member, a space between the window and a vascular wall will not be excessively pressed, so as to reserve enough selected space for the implantation of the bridging stent 100. In addition, before the implantation of the bridging stent 100, the blood supply of the branch vessel can be maintained all the time, which greatly reduces the probability of ischemic complications after surgery, and provides doctors with a plenty of operation time.

Embodiment II

Figure 10:
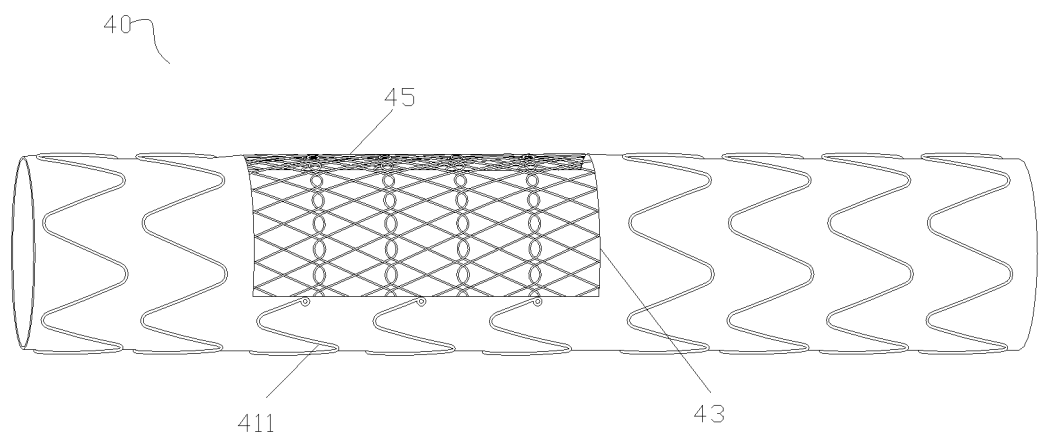
FIG. 10 is a schematic structural diagram of a covered stent according to one embodiment of the present disclosure, including a window supporting member.

As shown in FIG. 10, the structure of the covered stent 40 of this embodiment is roughly the same as that of the covered stent 10 of Embodiment I, and the difference is the window supporting member 45. The window supporting member 45 of this embodiment is formed separately, and the main body supporting member 411 opposite to the window supporting member 45 has an open structure, that is, the supporting members of other portions of the main body stent have a closed annular structure, while the main body supporting member 411 opposite to the window supporting member 45 is not a complete ring.

Figure 11:
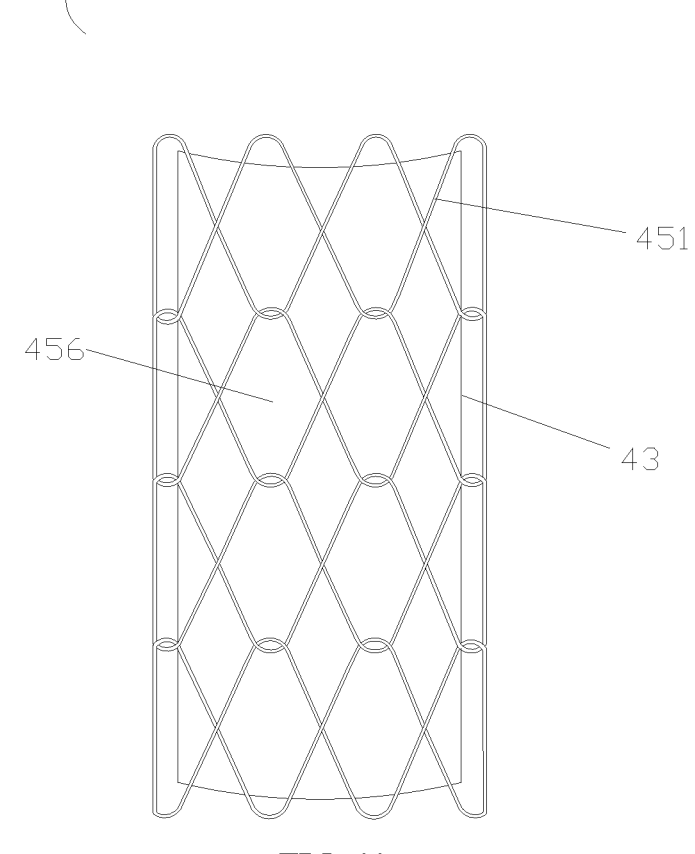
FIG. 11 is a schematic structural diagram of a window supporting member shown in FIG. 10.
Figure 12:
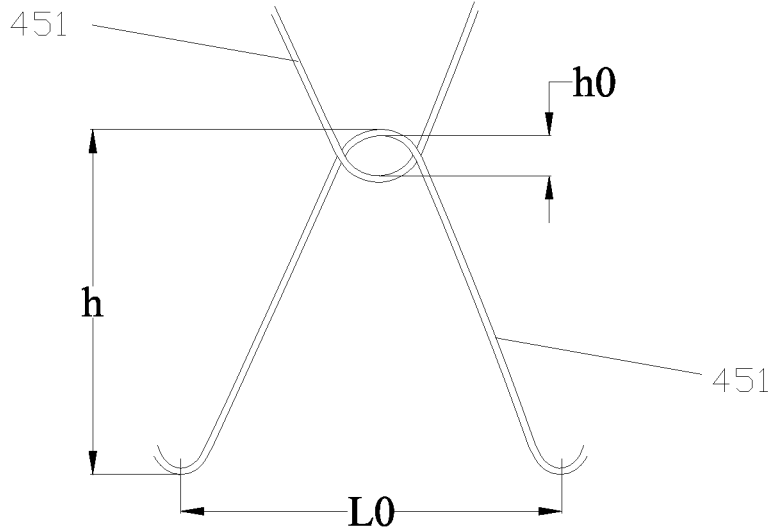
FIG. 12 is a partial schematic structural diagram of the window supporting member shown in FIG. 11.

As shown in FIG. 11 and FIG. 12, the window supporting member 45 of this embodiment includes a plurality of supporting sections 451. The plurality of supporting sections 451 is connected with an edge of a main body stent window 43, and the plurality of supporting sections 451 are connected by being hooked with each other to form a net structure with meshes 456. The net structure includes portions formed by braided wires. Intersections of the braided wires form vertices of the meshes 456. The vertices of the meshes 456 are formed by pressing or hooking the braided wires, so that the intersections of the braided wires are movable. Therefore, the size of each mesh can change by an external force. For example, when the bridging stent is implanted, an outer diameter of a sheath of a delivery device is greater than that of the mesh. At this time, the size of the mesh can increase under the pressure of the sheath, or when the outer diameter of the implanted bridging stent is greater than the size of the mesh, the braided wires will not press the bridging stent, and to some extent, can fix the position of the bridging stent to improve the stability of the implanted bridging stent to resist the impact of the blood flow.

As shown in FIG. 12, two adjacent supporting sections 451 are connected by means of being hooked to each other. That is, the wave crest of one supporting section 451 is connected with the wave trough of the other adjacent supporting section 451. The height h of a single supporting section 451 ranges from 6 to 20 mm, and the distance LO between adjacent wave crests or wave troughs of the single supporting section 451 is 10 to 25 mm, which can ensure that the space is not too small when the bridging stent is implanted. There is a certain distance h0 between the wave crests and wave troughs of two supporting sections 451 hooked to each other, which is between 0 mm and 5 mm. In this way, a certain stretching distance can be reserved between adjacent supporting sections. When the covered stent of this embodiment is implanted into a curved blood vessel, the window supporting member faces the large curvature side, so that there can be a certain stretching allowance between the multiple supporting sections 451, and the covered stent can better adapt to the curved blood vessel.

Preferably, in the circumferential direction, the same supporting section 451 includes two overlapping supporting rings, so that the meshes of the net structure are rhombic, and to some extent, the wall adherence and supporting performance of the window supporting member are improved. It can be understood that in other embodiments, the same supporting section can include a plurality of overlapping supporting rings. When there are more supporting rings, the size of the mesh is smaller. Therefore, the number of the overlapping supporting rings on the same supporting section is preferably 2 to 4.

In this embodiment, the window supporting member 45 partially overlaps the main body covering film of the main body stent, so as to facilitate the suturing of the window supporting member. At the same time, the window supporting member of the opening portion of the receiving cavity close to the folding portion can also play the role of a stiffener, which can ensure a good opening shape. It can be understood that in other embodiments, the window supporting member may not overlap the main body covering film in any portion. At this time, they can also be directly sutured with a suture.

It can also be understood that in other embodiments, the sum of the perimeter of a section of the window supporting member and the perimeter of a section of the main body stent opposite to the window supporting member is greater than the perimeter of the covering film on the section; that is, the window supporting member and the main body supporting member partially overlap in the circumferential direction. In this way, the wall adherence of the position of the window where the first and second edges are located and the supporting force of this portion can be properly enhanced, and the covered stent is not easy to collapse.

In this embodiment, the window supporting member 45 and the surface of the main body stent are naturally transitioned, that is, basically, any cross section of the covered stent 40 is basically equal.

Figure 13:
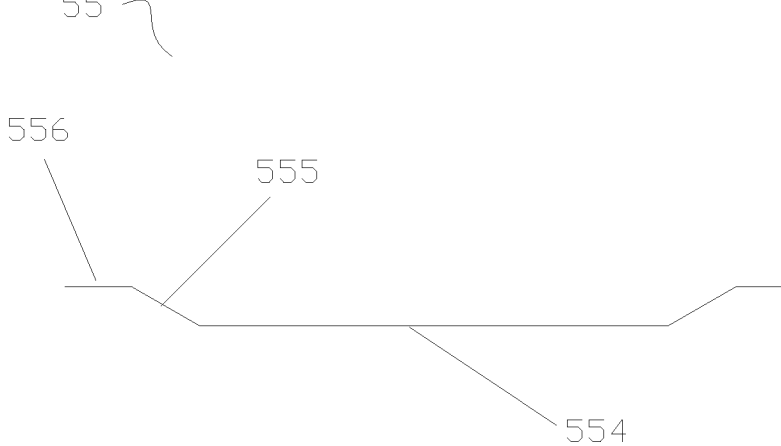
FIG. 13 is a schematic outline diagram of a window supporting member of a covered stent according to another embodiment of the present disclosure.
Figure 14:
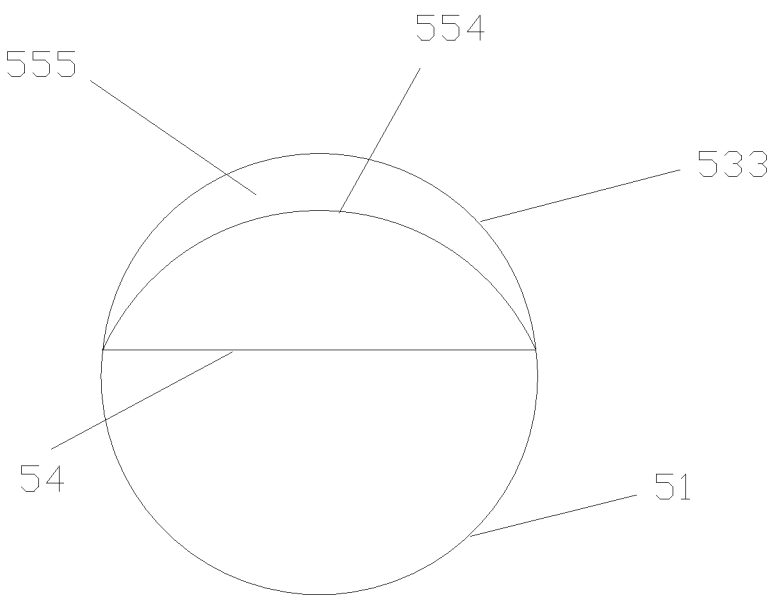
FIG. 14 is a diagram of a sectional outline of the covered stent shown in FIG. 13.

As shown in FIG. 13 and FIG. 14, in other embodiments, a sinking section 554 is formed on a surface of the window supporting member 55. The sinking section 554 is closer to the internal covering film than other portions of the window supporting member 55, so that an area of a cross section of the covered stent where the sinking section 554 is located is smaller than that of a cross section of other portions of the covered stent far away from the sinking section 554. Two ends connected with the sinking section 554 are also provided with a transition section 555 and a connecting section 556. The transition section 555 is a slope, which is arranged between the sinking section 554 and the connecting section 556. The connecting section 556 is connected with the main body stent, and is in the same curved surface with an outer surface of the main body stent. It can be understood that in other embodiments, the connecting section can also be excluded. At this time, the other end of the transition section is directly connected with the main body stent. Alternatively, in other embodiments, the transition section is a vertical plane. When the window supporting member of the covered stent has a sinking section, after the covered stent is implanted into the curved blood vessel, the deformation of the window supporting member is small, and the compression of the vascular wall at the large curvature side of the blood vessel is relatively small, so the counter-acting force of the window supporting member on the vascular wall is also reduced, making the long-term effect better after reconstruction of a diseased blood vessel, and secondary breaks and other problems will be avoided.

In other embodiments, the window supporting member and the main body supporting member on the opposite side can also be integrally braided and molded. At this time, the braiding density of the window supporting member can be controlled to be greater than that of the main body supporting member on the opposite side. In this way, the compliance of the whole covered stent (especially the position with the window) can be improved, and the wall adhesion of the position of the window provided with the first edge and the second edge can be also improved. Of course, in other embodiments, the window supporting member and the main body supporting member on the opposite side can also be braided separately, and the braiding density of the window supporting member is greater than that of the main body supporting member on the opposite side.

Embodiment III

Figure 15:
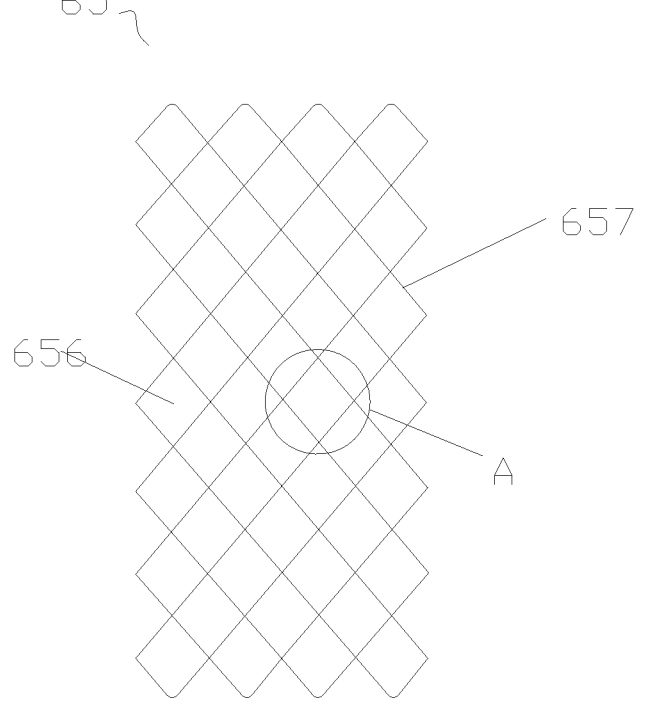
FIG. 15 is a schematic structural diagram of a window supporting member of a covered stent according to one embodiment of the present disclosure.
Figure 16:
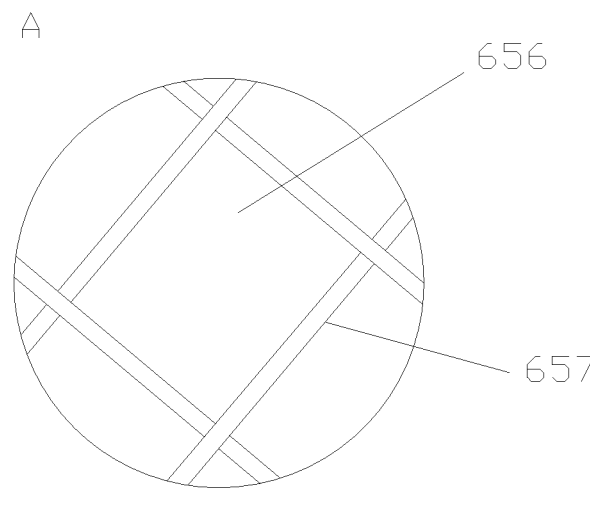
FIG. 16 is a partial enlarged structural diagram of the window supporting member shown in FIG. 15.

The structure of the covered stent of this embodiment is roughly the same as that of the covered stent of Embodiment II, and the difference is the window supporting member 65. As shown in FIG. 15 and FIG. 16, the window supporting member 65 of this embodiment is cross braided by braided wires 657, and a mesh 656 is of a rhombic structure. When the meshes 656 are formed, adjacent braided wires overlap each other to form movable intersections, so that four vertices of each mesh 656 are movable, and the range of the movement is wider than the range of movement of the movable intersections formed by mutual hooking. Therefore, this embodiment has no excessive restrictions on the size of the mesh. Even if the mesh is small, the mesh can adapt to the implantation of the bridging stent and play a role of stabilizing the bridging stent. In addition, the window supporting member of this embodiment does not have a structure similar to a wave crest or wave trough except at end portions. When the covered stent of this embodiment is applied to a curved blood vessel, the covered stent will irritate the blood vessel less.

Figure 17:
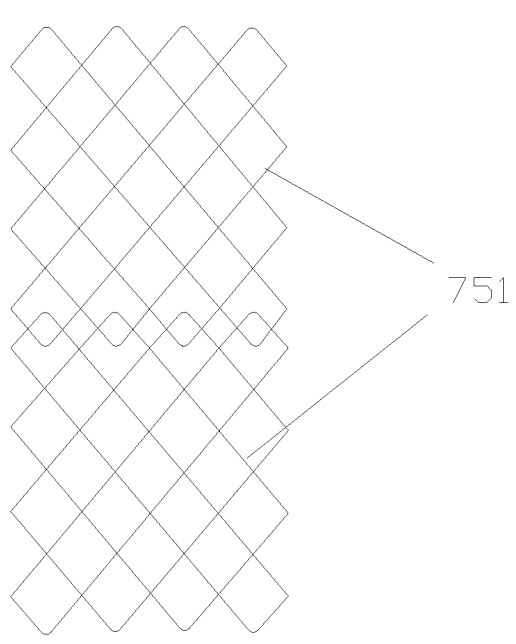
FIG. 17 is a schematic structural diagram of a window supporting member of a covered stent according to another embodiment of the present disclosure.

As shown in FIG. 17, in other embodiments, the window supporting member 75 can include at least two supporting sections 751. Adjacent supporting sections 751 are connected by mutual hooking. Each supporting section can be formed by cross braiding braided wires, that is, a net braided structure as shown in FIG. 15. At this time, since the adjacent supporting sections 751 are connected by mutual hooking, there can be a certain stretching allowance between the adjacent supporting sections 751, and the covered stent can better adapt to the curved blood vessel.

Embodiment IV

Figure 18:
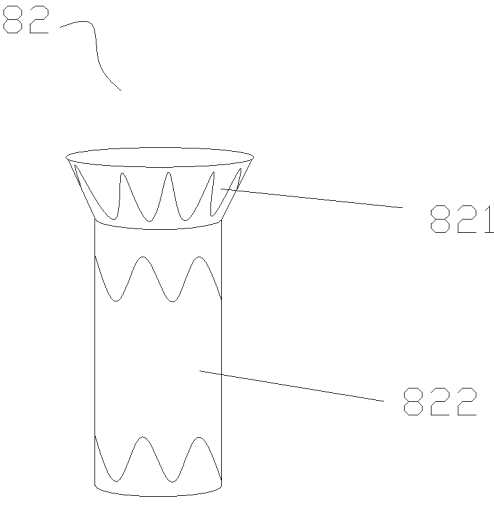
FIG. 18 is a schematic structural diagram of a branch stent of a covered stent according to one embodiment of the present disclosure.
Figure 19:
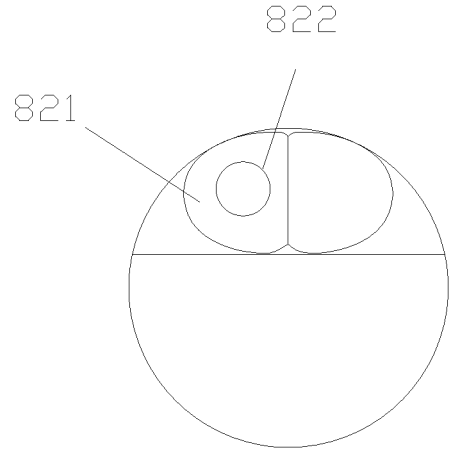
FIG. 19 is a side view of the covered stent including the branch stent shown in FIG. 18.

In Embodiment I, the branch stent has a hollow cylindrical structure. The branch stent of the covered stent of this embodiment is as shown in FIG. 18. Specifically, the branch stent 82 includes a first section 822 and a second section 821 connected with one end of the first section 822. The first section 822 has a cylindrical structure, and the second section 821 has a frustoconical structure. Both ends of the branch stent 82 are provided with openings communicating with an inner cavity of the branch stent. An opening of the first section 822 is larger than an opening of the second section 821, and the outer diameter of the second section 821 gradually decreases when extending from the opening to the first section 822 (that is, the first section 821 is a flared section). As shown in FIG. 19, on a cross section perpendicular to the central axis of the covered stent, a projection of the first section 822 falls into a projection of the second section 821. When the branch stent 82 of this embodiment is arranged between the proximal end of the window and the proximal end of the covered stent (that is, when the branch stent 82 communicates with the through hole at the proximal end of the internal covering film), an end of the first section 822 opposite the second section 821 is connected with the folding portion of the internal covering film, and an end of the second section 821 opposite to the first section 822 is a free end; that is, the first section 822 is a proximal end section of the branch stent, and the second section 821 is a distal end section of the branch stent. In contrast, when the branch stent 82 of this embodiment is arranged between the distal end of the window and the distal end of the covered bracket, the first section 822 is the distal end section of the branch stent, and the second section 821 is the proximal end section of the branch stent.

The branch stent 82 of this embodiment has the frustoconical first section, and the second section with a larger opening communicates with the through hole of the internal covering film, so that when a branch is selected, a guide wire or delivery device can easily enter the branch stent, and the bridging stent can be implanted more quickly.

Figure 20:
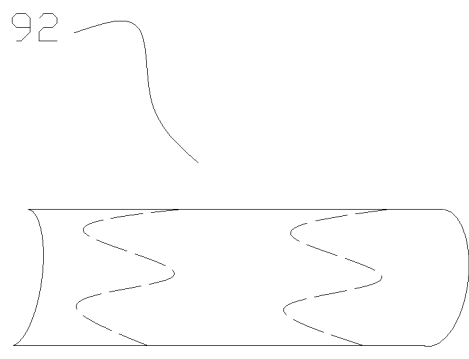
FIG. 20 is a schematic structural diagram of a branch stent of a covered stent according to another embodiment of the present disclosure.
Figure 21:
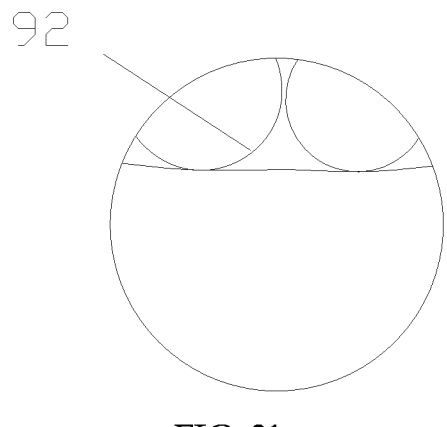
FIG. 21 is a side view of the covered stent including the branch stent shown in FIG. 20.

It can be understood that in other embodiments, the branch stent 92 may also be of an open structure. As shown in FIG. 20 and FIG. 21, the branch stent 92 is of a sheet structure with an arc surface, and the branch stent has a C-shaped cross section. Two edges between the proximal end and the distal end of the branch stent 92 are connected with an inner surface of the main body stent, so that a space enclosed by the branch stent 92 and the inner surface of the main body stent form an inner cavity of the branch stent 92. Since there is no other covering film between the inner cavity of the branch stent 92 and the inner surface of the main body stent, the materials of this portion are reduced, which reduces the overall thickness of this portion of the covered stent, and correspondingly reduces the difficulty of assembling the covered stent.

Figure 22:
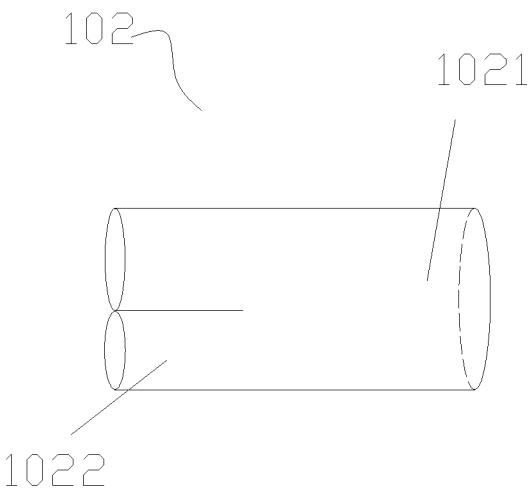
FIG. 22 is a schematic structural diagram of a branch stent of a covered stent according to still another embodiment of the present disclosure.
Figure 23:
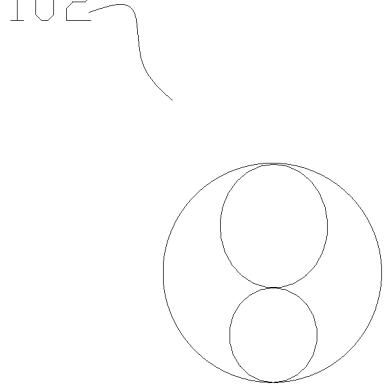
FIG. 23 is a side view of the covered stent including the branch stent shown in FIG. 22.

In other embodiments, when it is necessary to place two bridging stents at one end of the internal covering film, the branch stent can also adopt the structure shown in FIG. 22, that is, one end of the branch stent is provided with one opening, and the other end is provided with two openings. In combination with FIG. 22 and FIG. 23, the branch stent 102 overall has a hollow tubular structure, including a first section 1021 and a second section 1022. An end portion of the first section 1021 far away from the second section 1022 is provided with one opening, and an end portion of the second section 1022 far away from the first section 1021 is provided with two openings. The end portion of the first section 1021 far away from the second section 1022 is connected with the internal coating film, and the end portion of the second section 1022 far away from the first section 1021 is a free end. In this way, it is equivalent to having only one branch stent connected with the internal covering film, but two bridging stents can still be implanted, thus avoiding the internal hemorrhage caused by suturing between the openings of the branch stent.

It can be understood that in other embodiments, an extending direction of the branch stent arranged at the distal end of the internal covering film can form a certain angle with the length extending direction of the covered stent, and the included angle is greater than 0 degree. Alternatively, the branch stent connected to the distal end of the internal covering film can extend toward the central axis of the covered stent, so as to facilitate the implantation of the bridging stent of a branch vessel above the arch and reduce the curvature of the bridging stent.

Embodiment V

Figure 24:
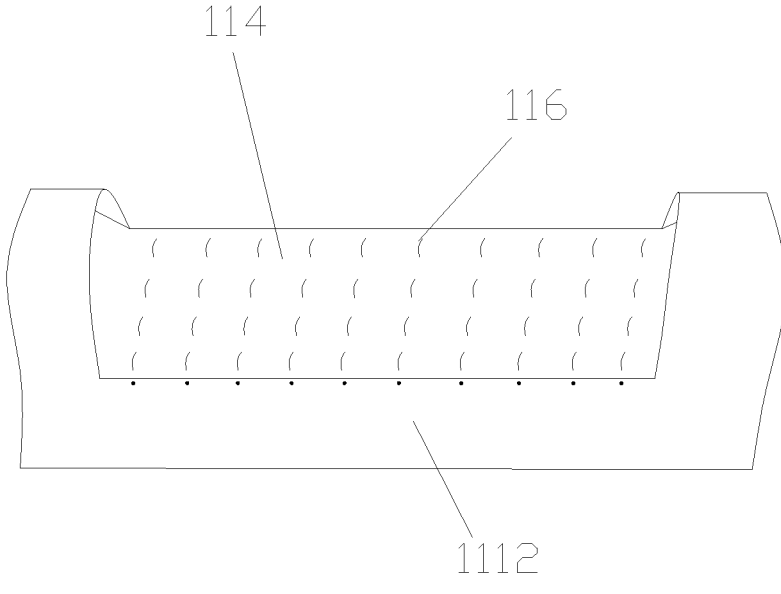
FIG. 24 is a partial schematic structural diagram of a covered stent according to one embodiment of the present disclosure.

The structure of the covered stent of this embodiment is roughly the same as that in Embodiment I, but the difference is the internal covering film. As shown in FIG. 24, the internal covering film 114 is provided with a supporting unit 116. The supporting unit 116 makes the bottom portion of the internal covering film at least partially parallel to a plane where the first edge and the second edge of the window are located, or protrude outwardly from the plane, or recessed inwardly relative to the plane.

Figure 25:
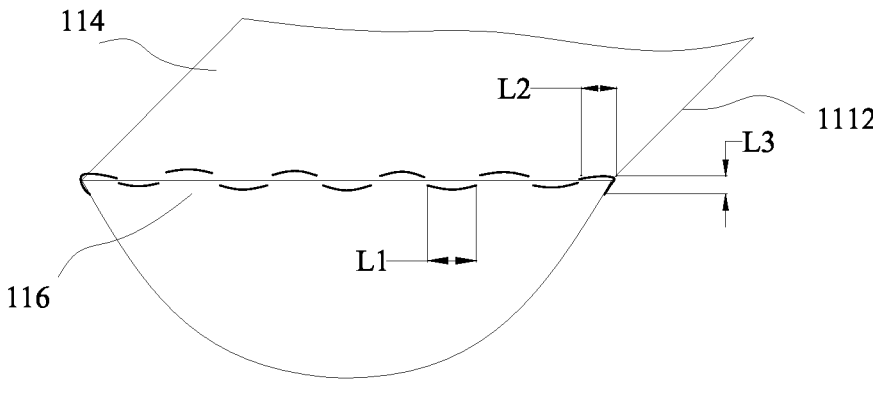
FIG. 25 is a partial schematic structural diagram of the covered stent shown in FIG. 24.

As shown in FIG. 25, in this embodiment, the supporting unit 116 includes a suture. The suture starts from a position of the main body covering film adjacent to the first edge of the window, then passes through upper and lower surfaces of the internal covering film 114 to the second edge of the window, bypasses the second edge and is fixed with the main body covering film 1112 of the main body stent; that is, the suture wraps around the internal covering film and edges of the main body covering film adjacent to the second edge and first edge of the window. The material of the suture can be a polymer material or a metal material, preferably a thinner flexible wire, so that the compression and loading of the covered stent will not be affected.

During suturing, the suture is threaded through the inner surface of the main body covering film to the outer surface of the main body covering film, then bypasses an edge of the main body covering film, passes through the internal covering film from the upper surface of the internal covering film to the lower surface of the internal covering film, and then goes back and forth on the internal covering film. Then, the suture is threaded through the inner surface of the internal covering film to the outer surface close to the second edge, then bypasses the main body covering film and an edge of the internal covering film, and passes through the outer surface of the main body covering film to the inner surface of the main body covering film, thus completing circumferential suturing of one section.

When the suture is threaded back and forth on the upper and lower surfaces of the internal covering film, a plurality of suture points is formed on the surfaces of the internal covering film. In order to reduce the impact of suture on an approach of the guide wire before the implantation of the bridging stent, the suture points shall not be too sparse. It is preferred that the distance $L2$ between two adjacent suture points is less than 2 mm; the distance $L3$ between the suture point close to the first or second edge of the window on the internal covering film 114 is also less than 2 mm; and the distance $L4$ between the suture point on the main body covering film 1112 and the first or second edge of the window is also less than 2 mm.

Figure 26:
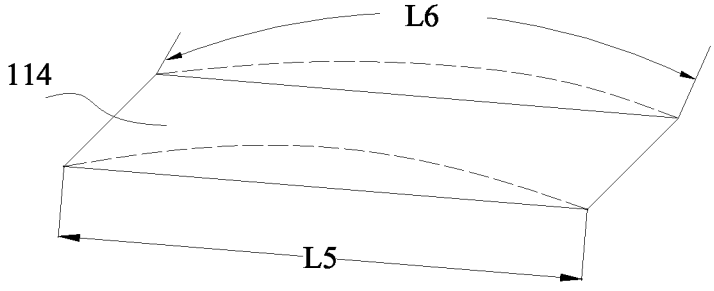
FIG. 26 is a schematic diagram of the states of an internal covering film before and after extension.

In addition, the supporting unit 116 improves the overall stability of the internal covering film 114 and reduces the deformation ability of the bottom portion of the internal covering film 114. As shown in FIG. 26, the axial length of the internal covering film 114 in a natural state is recorded as L5. The length of the internal covering film 114 when it is stretched under a force (for example, when the covered stent is applied to a curved blood vessel) is L6, and the elongation θ is a ratio of a length change of the internal covering film 114 before and after stretching to the length in the natural state. The existence of the supporting unit 116 limits the deformation of the internal covering film 114. In this embodiment, the elongation of the internal covering film is less than 0.1 and greater than 0.01. In this way, on the one hand, the internal covering film can adapt to the curved blood vessel without tearing, and on the other hand, it can be also ensured that the internal covering film will not deform excessively and collapse.

It can be understood that in other embodiments, the supporting unit of the internal covering film can also be a waveform supporting structure similar to the main body supporting unit, that is, the supporting unit is connected with a surface of the internal covering film by means of suturing or heat treatment after being formed separately. Alternatively, the supporting unit may be integrally braided with the window supporting member. As the waveform supporting structure has a certain wave height (i.e., axial length), the supporting unit has better integrity and has a better supporting effect and deformation limiting effect on the internal covering film. It can be understood that the supporting unit can also be integrally formed with the main body supporting member, or part of the supporting unit can be integrally formed with the main body supporting member, and part of the supporting unit can be integrally formed with the window supporting member. Alternatively, one part of the supporting unit and the main body supporting member are integrally formed, and one part of the window supporting member and the main body supporting member are integrally formed.

Preferably, the bottom portion of the internal covering film is convex or flat, which can ensure that the size of the inner cavity of the main body stent is not too small at the position with the internal covering film, so as not to affect the hemodynamics in the aorta.

In this embodiment, the internal covering film and the main body covering film are also spliced and connected after being formed separately. In this way, it is more convenient to manufacture the supporting unit on the internal covering film.

It can be understood that, in order to give consideration to the opening shape of the folding portion of the internal covering film, the opening of the folding portion can be slightly recessed, that is, the folding portion is closer to the central axis of the covered stent than the bottom portion, and the supporting unit can be only arranged at the bottom portion of the internal covering film. Since the axial length of the folding portion is obviously less than the axial length of the bottom portion, even if the folding portion is recessed, the hemodynamics flowing through the inner cavity of the main body stent will not be affected.

Embodiment VI

Figure 27:
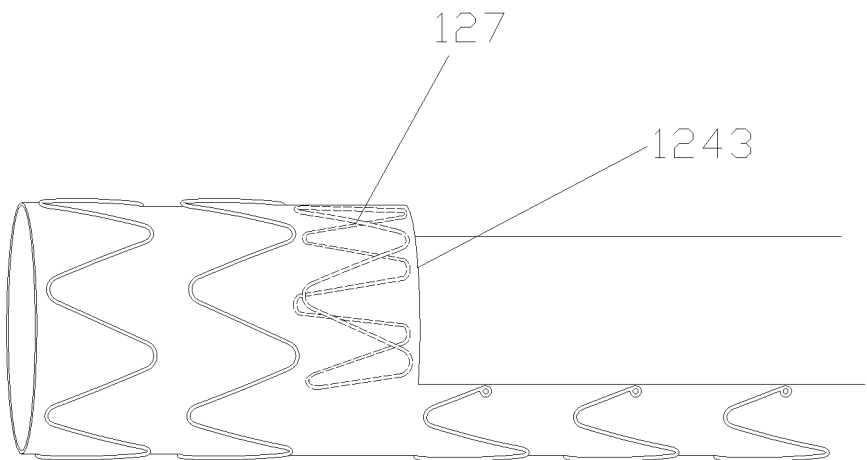
FIG. 27 is a partial schematic structural diagram of a covered stent according to one embodiment of the present disclosure, including a stiffener.
Figure 28:
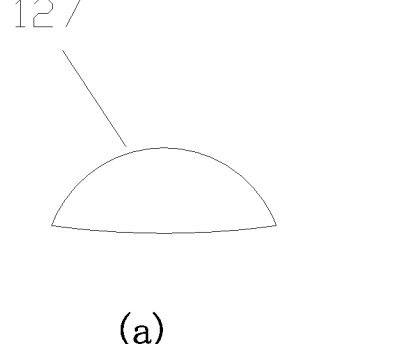
FIG. 28 shows several transformational structures of the stiffener shown in FIG. 27.
Figure 28:
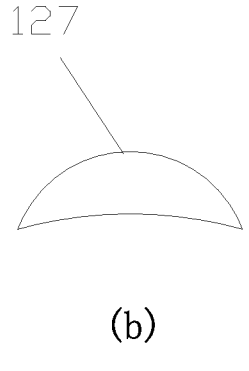
Figure 28:
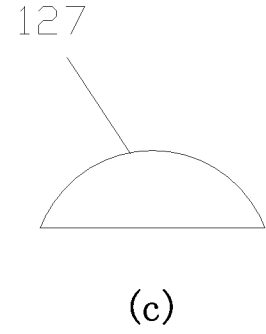

The structure of the covered stent of this embodiment is roughly the same as that of the covered stent of Embodiment II, and the difference is the stiffener of the folding portion. In order to better maintain a good opening shape of the folding portion, as shown in FIG. 27, the covered stent of this embodiment includes a stiffener 127. The stiffener 127 is arranged at the upper edge 1243 of the folding portion. In this embodiment, the stiffener 127 is a separate closed structure, which is arranged around the opening of the folding portion, supports the opening of the folding portion, and reduces the deformation ability of the opening. The stiffener 127 may be of a waveform structure similar to the main body supporting member, or of a closed structure enclosed by a metal wire. As shown in FIG. 28, when the stiffener 127 is of a closed structure, a portion connected with the upper edge 1243 of the folding portion is an arc adapting to the main body stent, and a portion opposite to the arc can be recessed toward the central axis of the covered stent, or can protrude outward from the central axis of the covered stent, or can be parallel to the central axes of the window and the covered stent.

It can be understood that in other embodiments, the stiffener can be a simple open structure, that is, the stiffener has two circumferential free ends or free edges. At this time, a projection of the stiffener on a cross section perpendicular to the central axis of the covered stent can be a curved surface, a curve, a plane or a straight-line segment. At this time, the stiffener can be arranged at any section of the opening of the folding portion, that is, the stiffener can be arranged on the upper surface (i.e. an upper folding unit) of the folding portion provided with the upper edge or the lower surface (i.e. a lower folding unit) of the folding portion opposite the upper edge, or can span the upper surface and the lower surface.

It can also be understood that the stiffener can be formed separately, or can be formed integrally with the window supporting member, or can be formed integrally with the main body supporting member.

The above specific embodiments are only some of the embodiments of the present disclosure, not a limitation of the present disclosure. This specification cannot enumerate all embodiments of the concept of the present disclosure. Some features of the above different embodiments can be replaced or combined with each other. Those skilled in the art can also make simple replacement according to actual needs. The concept of the present disclosure is subject to the claimed protection scope.

The invention claimed is:

1. A covered stent, comprising a main body stent, a window being formed on a surface of the main body stent, wherein the covered stent further comprises an internal covering film; an edge of the internal covering film is connected to the main body stent; the internal covering film comprises a bottom portion, a proximal end folding portion and a distal end folding portion, and the proximal end folding portion and distal end folding portion are disposed at two ends of the bottom portion, respectively; at least one of the proximal end folding portion and the distal end folding portion is disposed on an inner surface of the main body stent, and is recessed toward an inner cavity of the main body stent to form a receiving cavity; and a through hole that communicates with the inner cavity of the main body stent is also formed on the internal covering film.

2. The covered stent according to claim 1, wherein the through hole is arranged at a bottom portion of the receiving cavity, and the folding portion has an opening opposite to the through hole.

3. The covered stent according to claim 2, wherein the covered stent further comprises a stiffener; and the stiffener is at least partially arranged around the opening to support the opening of the folding portion.

4. The covered stent according to claim 3, wherein the stiffener is bent away from and/or close to a center of the opening.

5. The covered stent according to claim 2, wherein the main body stent comprises a main body supporting member, and an edge of an opening of the receiving cavity partially overlaps the main body supporting member.

6. The covered stent according to claim 2, wherein the stiffener comprises a suture; the opening of the folding portion comprises an upper edge; and the upper edge and an edge of the window are sutured through the suture.

7. The covered stent according to claim 1, wherein two ends of the covered stent are provided with openings; the receiving cavity comprises an opening and a through hole;
  the opening of the receiving cavity is opposite to the openings of the covered stent; and the size of the receiving cavity gradually decreases along the direction from the opening of the folding portion to an opening of the covered stent.

8. The covered stent according to claim 1, wherein the covered stent further comprises a branch stent; and the branch stent is arranged inside the covered stent and communicates with the through hole of the internal covering film.

9. The covered stent according to claim 8, wherein the branch stent comprises a flared section; and the flared section is connected with the internal covering film.

10. The covered stent according to claim 8, wherein the branch stent has a sheet structure with an arc surface; the branch stent has a C-shaped cross section, and is arranged on an inner surface of the main body stent; and the space enclosed by the branch stent and the inner surface of the main body stent forms an inner cavity of the branch stent.

11. The covered stent according to claim 8, wherein one end of the branch stent is provided with an opening, and the other end is provided with two openings; and an end portion of the branch provided with one opening is connected with the internal covering film.

12. The covered stent according to claim 1, wherein the covered stent further comprises a window supporting member; the window supporting member is arranged outside the internal covering film and protrudes outwardly from a surface of the internal covering film; the window supporting member comprises a net structure with meshes, and the size of each mesh is changeable by an external force.

13. A covered stent, comprising a main body covering film, and a window formed on a surface of the main body covering film, wherein the covered stent further comprises an internal covering film; an edge of the internal covering film is connected with the main body covering film; and the internal covering film and the main body covering film are spliced and connected after being formed separately.

14. The covered stent according to claim 13, wherein the window comprises a first edge and a second edge extending along a longitudinal direction of the covered stent; the internal covering film comprises a bottom portion located between the first edge and the second edge; the internal covering film is provided with a supporting unit; and the supporting unit makes the bottom portion at least partially protrude outwardly or is partially recessed relative to a plane where the first edge and the second edge are located, or parallel to the plane.

15. The covered stent according to claim 14, wherein the supporting unit comprises a suture; and the suture bypasses the first edge and an edge of the internal covering film, passes through upper and lower surfaces of the internal covering film to the second edge, then bypasses the second edge and the other edge of the internal covering film, and then is connected with the internal covering film and the main body stent.

16. The covered stent according to claim 13, wherein the elongation of the internal covering film is greater than 0.01 and less than 0.1.

17. The covered stent according to claim 14, wherein the supporting unit comprises a waveform supporting structure; and the waveform supporting structure is connected with the surface of the internal covering film.

18. The covered stent according to claim 17, wherein the covered stent further comprises a window supporting member; the window supporting member is arranged outside the internal covering film and protrudes outwardly from the surface of the internal covering film; and the waveform supporting structure is integrally formed with the window supporting member.

19. The covered stent according to claim 14, wherein the internal covering film comprises a bottom portion, a proximal end folding portion and a distal end folding portion;
  the proximal end folding portion and the distal end folding portion are arranged at two ends of the bottom portion respectively; at least one of the proximal end folding portion and the distal end folding portion is arranged on an inner surface of the main body covering film; the supporting unit is arranged at the bottom portion; and the folding portion is closer to a central axis of the covered stent than the bottom portion.

20. The covered stent according to claim 18, wherein a sinking section is formed on a surface of the window supporting member, and the area of a cross section of the covered stent where the sinking section is located is smaller than areas of cross sections of other portions of the covered stent far from the sinking section.

* * * * *